(12) United States Patent
Sabharwal et al.

(10) Patent No.: US 11,521,713 B2
(45) Date of Patent: Dec. 6, 2022

(54) SYSTEM AND METHOD FOR GENERATING CLINICAL TRIAL PROTOCOL DESIGN DOCUMENT WITH SELECTION OF PATIENT AND INVESTIGATOR

(71) Applicant: HCL TECHNOLOGIES LIMITED, Noida (IN)

(72) Inventors: Navin Sabharwal, Noida (IN); Amit Agrawal, Noida (IN)

(73) Assignee: HCL TECHNOLOGIES LIMITED

( * ) Notice: Subject to any disclaimer, the term of this patent is extended or adjusted under 35 U.S.C. 154(b) by 779 days.

(21) Appl. No.: 16/414,618

(22) Filed: May 16, 2019

(65) Prior Publication Data
US 2020/0365239 A1    Nov. 19, 2020

(51) Int. Cl.
*G16H 10/20* (2018.01)
*G06K 9/62* (2022.01)
(Continued)

(52) U.S. Cl.
CPC .......... *G16H 10/20* (2018.01); *G06F 40/295* (2020.01); *G06K 9/6218* (2013.01); *G06N 3/0454* (2013.01); *G06N 20/00* (2019.01)

(58) Field of Classification Search
CPC ... G06F 1/00–2221/2153; G16H 10/00–80/00; G06K 1/00; G06K 2215/111; G06N 3/00–99/007
See application file for complete search history.

(56) References Cited

U.S. PATENT DOCUMENTS

| 7,054,823 B1 * | 5/2006 | Briegs ................ G06Q 10/0637 707/999.001 |
| 8,504,380 B2 | 8/2013 | Broverman et al. |

(Continued)

FOREIGN PATENT DOCUMENTS

| EP | 3311317 A1 | 4/2018 |
| FR | 3067142 A1 | 12/2018 |
| WO | WO-0157739 A1 * | 8/2001 ............. G06F 16/24 |

OTHER PUBLICATIONS

Dhaya Sindhu Battina, "The Role of Machine Learning in Clinical Research: Transforming the Future of Evidence Generation," Novateur Publications International Journal of Innovations in Engineering Research and Technology [IJIERT] ISSN: 2394-3696 (Year: 2017).*

*Primary Examiner* — Jonathon A. Szumny
(74) *Attorney, Agent, or Firm* — Kendal Sheets

(57) ABSTRACT

Disclosed is a system for generating Clinical trial protocol design document with selection of a Patient and an Investigator for a clinical trial process. The system inputs meaningful information derived from the raw data, a pre-Drafted protocol, a regulatory authorities' protocol curated by regulatory authorities, and a pre-stored dataset, present in a repository. A Clinical trial protocol design document is drafted by generating a case frame upon extracting data in form of a key value into a standard document. Each key value is validated and a prediction score is computed based on overlapping of the interim Clinical trial protocol design template with the pre-Drafted protocol and the regulatory authorities' protocol to determine whether the interim Clinical trial protocol design document is approved or rejected. A Clinical trial protocol design document is generated when the interim Clinical trial protocol design document is approved.

11 Claims, 8 Drawing Sheets

(51) Int. Cl.
    *G06N 20/00*    (2019.01)
    *G06N 3/04*     (2006.01)
    *G06F 40/295*   (2020.01)

(56) References Cited

U.S. PATENT DOCUMENTS

| | | | |
|---|---|---|---|
| 2009/0063428 A1* | 3/2009 | Meier | G16H 10/20 |
| 2009/0313048 A1* | 12/2009 | Kahn | G16H 15/00 |
| | | | 703/11 |
| 2012/0072232 A1 | 3/2012 | Frankham et al. | |
| 2013/0132112 A1* | 5/2013 | Sablinski | G16H 70/60 |
| | | | 705/2 |
| 2013/0197894 A1* | 8/2013 | Sablinski | G16H 10/20 |
| | | | 703/11 |
| 2014/0316793 A1 | 10/2014 | Pruit | |
| 2015/0286802 A1* | 10/2015 | Kansara | G16H 10/20 |
| | | | 705/3 |
| 2016/0125171 A1* | 5/2016 | Finken | G06F 16/285 |
| | | | 705/2 |
| 2017/0351814 A1 | 12/2017 | Fink et al. | |
| 2018/0301205 A1 | 10/2018 | Mao | |
| 2019/0206521 A1* | 7/2019 | Walpole | G16H 15/00 |
| 2020/0286596 A1* | 9/2020 | Yang | G16H 70/20 |
| 2020/0303069 A1* | 9/2020 | Mulligan | G16H 50/70 |
| 2021/0257061 A1* | 8/2021 | Li | G16H 15/00 |

\* cited by examiner

SYSTEM AND METHOD FOR GENERATING CLINICAL TRIAL PROTOCOL DESIGN DOCUMENT WITH SELECTION OF PATIENT AND INVESTIGATOR

CROSS REFERENCE TO RATED APPLICATIONS

This patent application does not claim priority from any application.

TECHNICAL FIELD

The present invention described herein, in general, relates to the field of Information Technology. More specifically, the present invention is an Artificial Intelligence (AI) system that generates a clinical trial protocol design document with selection of a Patient and an Investigator.

Currently, most of the tasks undertaken in a protocol design are manual extraction of information from multiple sources and generating protocol designs out of historical data inputs and other input sources. Since it is a manual task, there is a high probability of pulling sub-par choices at various steps due to lack of information or missing out inputs from archived sources of the institution. The impacts of such cases may be huge since any poorly constructed protocol results in sub-optimal implementations with respect to operational stand point. Additionally, impact on data quality may prove to be costly, involve delays and cross team inefficacy.

Further, it has been observed that Trial Planning and Designing may become very time consuming, erroneous, may lead to unnecessary consumption of resources. This is because consolidation of data from various input sources involves manual intervention. Cross communication of information between a Subject Matter Expert (SME) is also a challenge and at times may cause data inconsistencies. Furthermore, the manual sources also indirectly lead to inconsistencies in the data due to the differences in format and metadata.

SUMMARY

Before the present systems and methods, are described, it is to be understood that this application is not limited to the systems, and methodologies described, as there can be multiple possible embodiments which are not expressly illustrated in the present disclosure. It is also to be understood that the terminology used in the description is for describing the versions or embodiments only, and is not intended to limit the scope of the present application. This summary is provided to introduce concepts related to systems and methods for generating Clinical trial protocol design document thereby selecting a Patient and an Investigator for a clinical trial process and the concepts are further described below in the detailed description. This summary is not intended to identify essential features of the claimed subject matter nor is it intended for use in limiting the scope of the claimed subject matter.

In one implementation, a system for generating Clinical trial protocol design document thereby selecting a Patient and an Investigator for a clinical trial process is disclosed. The system may comprise a processor and a memory coupled to the processor. The processor may execute a plurality of modules present in the memory. The plurality of modules may comprise a Trial Planning and Design module, a Draft Protocol Development and Approval module, and an Investigator's Selection and Patient Recruitment module. The Trial Planning and Design module may acquire raw data, from a plurality of disparate data sources, comprising a set of documents. It may be noted that the raw data is being pre-processed to deduce meaningful information. The Trial Planning and Design module may further input the meaningful information, a pre-Drafted protocol, a regulatory authorities protocol curated by regulatory authorities, and a pre-stored dataset, present in a repository coupled with the processor. In one aspect, the pre-stored dataset may comprise queries, pre-asked queries by the regulatory authorities mapped with responses to the pre-asked queries. The Draft Protocol Development and Approval module may draft a Clinical trial protocol design document by generating a case frame upon extracting data in form of a key value, from the pre-Drafted protocol and the regulatory authorities protocol, into a standard document. Post generation of the case frame, each key value may be validated with the pre-asked queries and the responses to compute a predictive value, corresponding to each key value. In one aspect, the predictive value computed for each key value facilitates to draft an interim Clinical trial protocol design document. After drafting the interim Clinical trial protocol design document, a prediction score may be computed based on overlapping of the interim Clinical trial protocol design document with the pre-Drafted protocol and the regulatory authorities protocol to determine whether the interim Clinical trial protocol design document is approved or rejected. When the interim Clinical trial protocol design document is approved based on the prediction score and further approved by the regulatory authorities, the Clinical trial protocol design document may be generated. The Investigator's Selection and Patient Recruitment module may select an investigator, for performing the clinical trial, and a patient on which the clinical trial needs to be performed. In one aspect, the selection may be performed based on set of parameters. In one aspect, the set of parameters may comprise correlation between features, associated to the Clinical trial protocol design document, and features associated to a profile of the investigator or features associated to a profile of the patent, past trials undertaken by investigators, social networking data, historical data of the patient.

In another implementation, a method for generating Clinical trial protocol design document thereby selecting a Patient and an Investigator for a clinical trial process is disclosed. In order to generate the Clinical trial protocol design document and selecting the Patient and the Investigator, initially, raw data may be acquired from a plurality of disparate data sources comprising a set of documents, wherein the raw data is being pre-processed to deduce meaningful information. After the acquisition of the raw data, the meaningful information, a pre-Drafted protocol, a regulatory authorities protocol curated by regulatory authorities, and a pre-stored dataset may be inputted. In one aspect, the pre-stored dataset may comprise queries, pre-asked queries by the regulatory authorities mapped with responses to the pre-asked queries. Post inputting the meaningful information, a Clinical trial protocol design document may be drafted. In one embodiment, the Clinical trial protocol design document may be drafted by generating a case frame upon extracting data in form of a key value, from the pre-Drafted protocol and the regulatory authorities protocol, into a standard document, validating each key value with the pre-asked queries and the responses to compute a predictive value, corresponding to each key value, thereby drafting an interim Clinical trial protocol design document based the predictive value computed for each key value, computing a prediction score based on overlapping of the interim Clinical trial protocol design document with the pre-Drafted protocol and the regulatory authorities protocol to determine whether the interim Clinical trial protocol design document is approved or rejected, and generating the Clinical trial protocol design document, when the interim Clinical trial protocol design document is approved based on the prediction score and further approved by the regulatory authorities. Further, an investigator, for performing the clinical trial, and a patient, on which the clinical trial needs to be performed may be selected based on a set of parameters. The set of parameters may comprise correlation between features, associated to the Clinical trial protocol design document, and features associated to a profile of the investigator or features associated to a profile of the patent, past trials undertaken by investigators, social networking data, historical data of the patient. In one aspect, the aforementioned method for generating the Clinical trial protocol design document thereby selecting the Patient and the Investigator may be performed by a processor using programmed instructions stored in a memory.

In yet another implementation, non-transitory computer readable medium embodying a program executable in a computing device for computing device for generating Clinical trial protocol design document thereby selecting a Patient and an Investigator for a clinical trial process is disclosed. The program may comprise a program code for acquiring raw data, from a plurality of disparate data sources comprising a set of documents, wherein the raw data is being pre-processed to deduce meaningful information. The program may further comprise a program code for inputting the meaningful information, a pre-Drafted protocol, a regulatory authorities protocol curated by regulatory authorities, and a pre-stored dataset, present in a repository coupled with the processor, wherein the pre-stored dataset comprises queries, pre-asked queries by the regulatory authorities mapped with responses to the pre-asked queries. The program may further comprise a program code for drafting a Clinical trial protocol design document by generating a case frame upon extracting data in form of a key value, from the pre-Drafted protocol and the regulatory authorities protocol, into a standard document, validating each key value with the pre-asked queries and the responses to compute a predictive value, corresponding to each key value, thereby drafting an interim Clinical trial protocol design document based the predictive value computed for each key value, computing a prediction score based on overlapping of the interim Clinical trial protocol design document with the pre-Drafted protocol and the regulatory authorities protocol to determine whether the interim Clinical trial protocol design document is approved or rejected, and generating the Clinical trial protocol design document, when the interim Clinical trial protocol design document is approved based on the prediction score and further approved by the regulatory authorities. The program may further comprise a program code for selecting an investigator, for performing the clinical trial, and a patient, on which the clinical trial needs to be performed, based on a set of parameters, wherein the set of parameters comprises correlation between features, associated to the Clinical trial protocol design document, and features associated to a profile of the investigator or features associated to a profile of the patent, past trials undertaken by investigators, social networking data, historical data of the patient.

BRIEF DESCRIPTION OF THE DRAWINGS

The foregoing detailed description of embodiments is better understood when read in conjunction with the appended drawings. For illustrating the disclosure, example constructions of the disclosure are shown in the present document; however, the disclosure is not limited to the specific methods and apparatus disclosed in the document and the drawings.

The detailed description is given with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
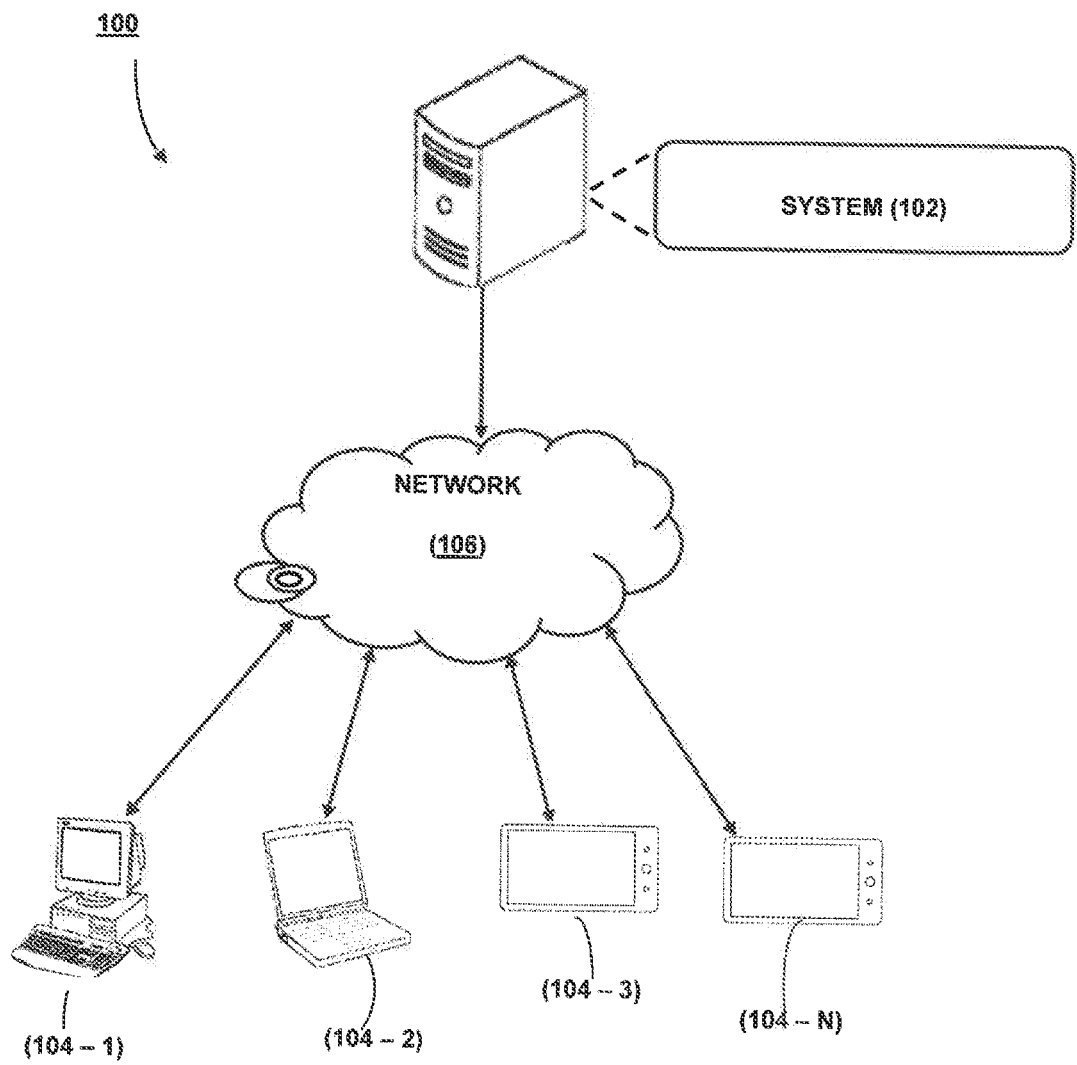
FIG. 1 illustrates a network implementation of a system for generating clinical trial protocol design thereby selecting a Patient and an Investigator for a clinical trial process, in accordance with an embodiment of the present subject matter.

Some embodiments of this disclosure, illustrating all its features, will now be discussed in detail. The words "comprising," "having," "containing," and "including," and other forms thereof are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any systems and methods similar or equivalent to those described herein can be used in the practice, the exemplary, systems and methods am now described. The disclosed embodiments are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure is not intended to be limited to the embodiments illustrated, but is to be accorded the widest scope consistent with the principles and features described herein.

It may be noted that Designing and framing of Protocols in any environment like Clinical trial protocol design document is mostly a manual labour intensive task and require a lot of effort from multiple sources. An inefficient or over complex design pattern on any day cost the data quality being retrieved. As a solution to propose, Artificial Intelligence (AI) and Machine Learning (ML) techniques may have huge applications in understanding the environment of Protocol Design in a clinical trial process, analysing the requirement to construct the Protocol Design, fulfillment of the Protocol Design's requirement and involving a Subject Matter Expert (SME) inputs to enable better accuracy of results being achieved and thereby making the system more intelligent for providing better results without any manual intervention.

The analogical implementation of the present invention for the use case of Smart Protocol Design has four main components including a Trial Planning and Design, Draft Protocol Development and Approval, an Investigator's Selection and a Patient Recruitment. The Trial Planning and Design includes acquisition of raw data, from a plurality of disparate data sources comprising a set of documents and inputting the meaningful information, a pre-Drafted protocol, a regulatory authorities protocol curated by regulatory authorities, and a pre-stored dataset. It may be noted that the raw data is being pre-processed to deduce meaningful information and the pre-stored dataset comprises queries, pre-asked queries by the regulatory authorities mapped with responses to the pre-asked queries.

The Draft Protocol Development and Approval includes drafting a Clinical trial protocol design document by a) generating a case frame upon extracting data in form of a key value, from the pre-Drafted protocol and the regulatory authorities protocol, into a standard document, b) validating each key value with the pre-asked queries and the responses to compute a predictive value corresponding to each key value thereby drafting an interim Clinical trial protocol design document based the predictive value computed for each key value, c) computing a prediction score based on overlapping of the interim Clinical trial protocol design document with the pre-Drafted protocol and the regulatory authorities protocol to determine whether the interim Clinical trial protocol design document is approved or rejected, and d) generating the Clinical trial protocol design document, when the interim Clinical trial protocol design document is approved based on the prediction score and further approved by the regulatory authorities.

The Investigator's Selection and the Patient Recruitment include selection of an investigator, for performing the clinical trial, and a patient on which the clinical trial needs to be performed. In one aspect, the investigator and the patient may be selected based on a set of parameters including, but not limited to, correlation between features, associated to the Clinical trial protocol design document, and features associated to a profile of the investigator or features associated to a profile of the patent, past trials undertaken by investigators, social networking data, historical data of the patient.

Thus, in this manner, the present system facilitates to generate the Clinical trial protocol design document thereby selecting the Patient and the Investigator for the clinical trial process.

Referring now to FIG. 1, a network implementation 100 of a system 102 for generating a Clinical trial protocol design document thereby selecting a Patient and an Investigator for a clinical trial process is disclosed. In order to generate the Clinical trial protocol design document and selecting the Patient and the Investigator, initially, the system 102 acquires raw data from a plurality of disparate data sources comprising a set of documents. It may be noted that the raw data is being pre-processed to deduce meaningful information. After the acquisition of the raw data, the system 102 inputs the meaningful information, a pre-Drafted protocol, a regulatory authorities protocol curated by regulatory authorities, and a pre-stored dataset. Post inputting the meaningful information, the system 102 drafts a Clinical trial protocol design document by generating a case frame upon extracting data in form of a key value, from the pre-Drafted protocol and the regulatory authorities protocol, into a standard document, validating each key value with the pre-asked queries and the responses to compute a predictive value, corresponding to each key value, thereby drafting an interim Clinical trial protocol design document based the predictive value computed for each key value, computing a prediction score based on overlapping of the interim Clinical trial protocol design document with the pre-Drafted protocol and the regulatory authorities protocol to determine whether the interim Clinical trial protocol design document is approved or rejected, and generating the Clinical trial protocol design document, when the interim Clinical trial protocol design document is approved based on the prediction score and further approved by the regulatory authorities. Further, the system 102 selects an investigator, for performing the clinical trial, and a patient on which the clinical trial needs to be performed. In one aspect, the system 102 selects the investigator and the patient based on a set of parameters.

Although the present disclosure is explained considering that the system 102 is implemented on a server, it may be understood that the system 102 may be implemented in a variety of computing systems, such as a laptop computer, a desktop computer, a notebook, a workstation, a mainframe computer, a server, a network server, a cloud-based computing environment. It will be understood that the system 102 may be accessed by multiple users through one or more user devices 104-1, 104-2 . . . 104-N, collectively referred to as user 104 or stakeholders, hereinafter, or applications residing on the user devices 104. In one implementation, the system 102 may comprise the cloud-based computing environment in which a user may operate individual computing systems configured to execute remotely located applications. Examples of the user devices 104 may include, but are not limited to, an Internet-of-Things (IoT) device, IoT gateway, portable computer, a personal digital assistant, a handheld device, and a workstation. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Hypertext Transfer Protocol Secure (HTTPS), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
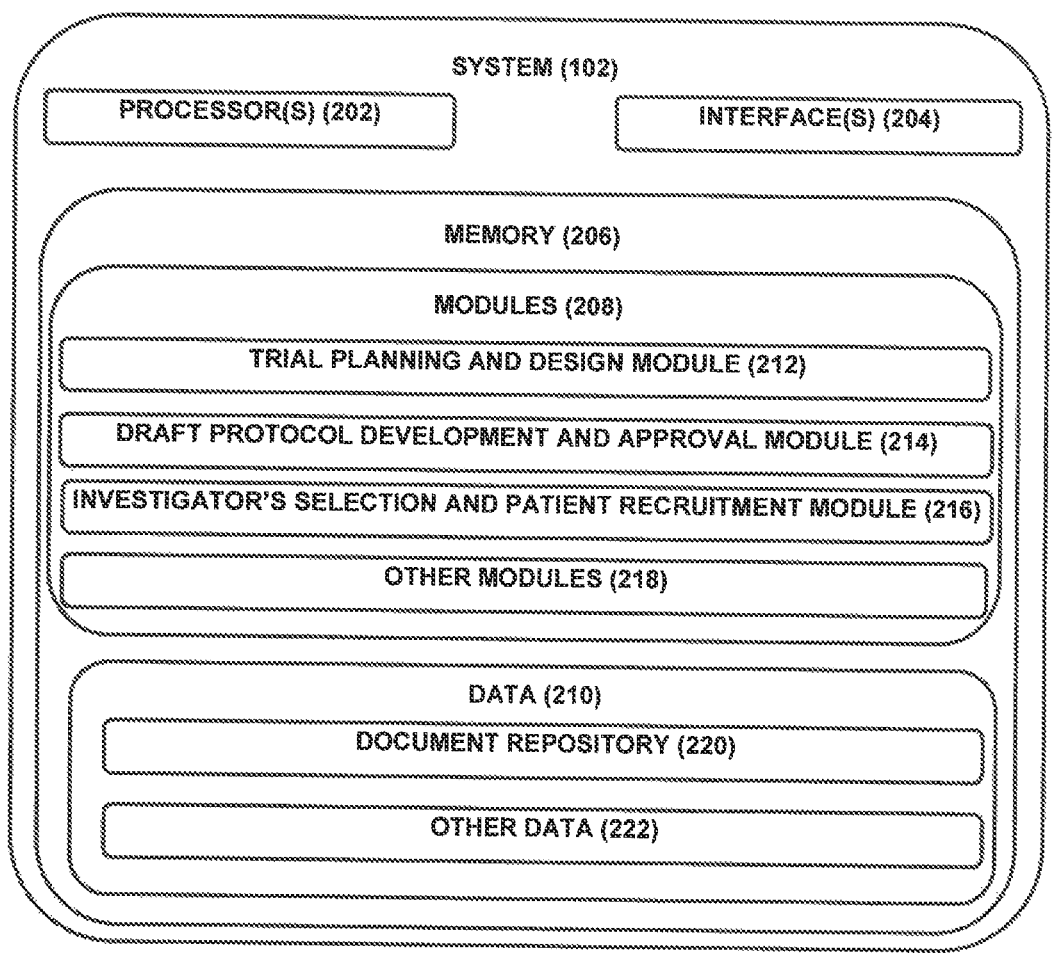
FIG. 2 illustrates the system, in accordance with an embodiment of the present subject matter.

Referring now to FIG. 2, the system 102 is illustrated in accordance with an embodiment of the present subject matter. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with the user directly or through the user devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 210.

The modules 208 include routines, programs, objects, components, data structures, etc., which perform particular tasks or implement particular abstract data types. In one implementation, the modules 208 may include a Trial Planning and Design module 212, a Draft Protocol Development and Approval module 214, and an Investigator's Selection and Patient Recruitment module 216. The other modules 218 may include programs or coded instructions that supplement applications and functions of the system 102. The modules 208 described herein may be implemented as software modules that may be executed in the cloud-based computing environment of the system 102.

The data 210, amongst other things, serves as a repository for storing data processed, received, and generated by one or more of the modules 208. The data 210 may also include a document repository 220 and other data 222. The other data 222 may include data generated as a result of the execution of one or more modules in the other modules 218.

As there are various challenges observed in the existing art, the challenges necessitate the need to build the system 102 for generating a Clinical trial protocol design document thereby selecting a Patient and an Investigator for a clinical trial process. In order to generate the Clinical trial protocol design document thereby selecting the Patient and the Investigator, the system 102 may comprise the Trial Planning and Design module 212, the Draft Protocol Development and Approval module 214, and the Investigator's Selection and Patient Recruitment module 216. The detail functioning of these modules is given below.

It may be noted that the Trial Planning and Design module 212 is used for data acquisition. The data acquisition is a very important step because from this point, the system 102 tends to incorporate all existing information that may be useful in solution construction. The Trial Planning and Design module 212 acquires raw data, from a plurality of disparate data sources, comprising a set of documents. The plurality of disparate data sources includes sources that contain domain information related documents, Literature Survey on the Problem Statement, Regulatory Body Repository, and Internal Repository.

Figure 3:
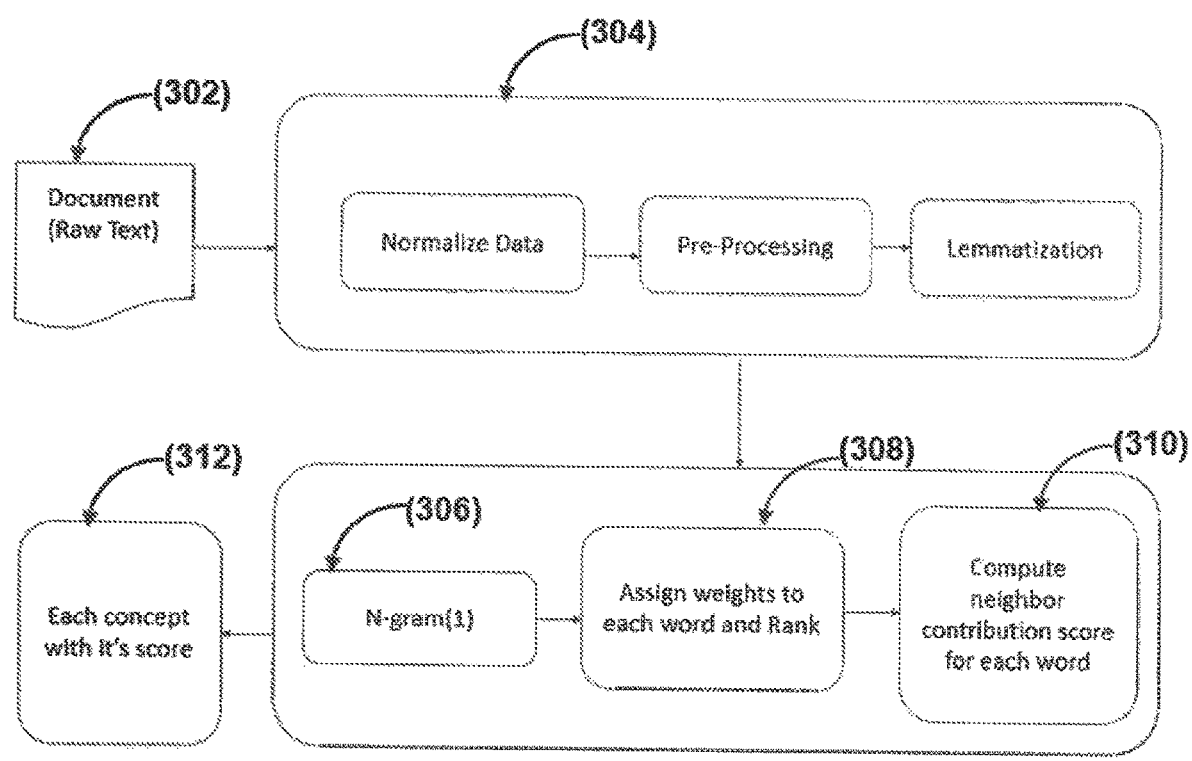
FIGS. 3 to 6 illustrate various implementations of the system for generating the clinical trial protocol design thereby selecting the Patient and the Investigator.

Referring to FIG. 3, once the raw data 302 is being acquired from the aforementioned disparate data sources, the Trial Planning and Design module 212 pre-processes the raw data 302 to deduce meaningful information, as shown in block 304. In order to deduce the meaningful information, the raw data 302 is then broken down to extract all important information, checking for data consistency, variedness, sufficiency and all other important pre-requisites. In other words, the meaningful information may be deduced by performing at least one of Text Processing, Data Processing, Concept Extraction, Summarizing, Clustering, Topic Modelling, Indexing, and Learning to Rank.

Text processing includes removing at least one of stop word and a special character from each document of the set of documents thereby generating one or more lemmas to make the raw data executable for Natural Language Processing (NLP) technique. This step is a prerequisite to enable any Natural Language processing on processed data, as shown in block 304.

Data Processing includes further processing the processed data to identify a plurality of Named Entity from the raw data 302, upon executing the NLP technique, to determine a domain pertaining to each document. Since the processed data being provided is mostly domain restricted and may not share scope with general taxonomies and identities, Custom Named Entity Recognizers need to be constructed that take in feeds from Domain rich information, Taxonomies etc. and extract the plurality of Named Entity from the processed data. It may be noted that plurality of Named Entity may also pose some relations between one another.

Based on the processing on the raw, as aforementioned, a concept is extracted along with a score 312. In one aspect, the concept is extracted by performing at least one of an N-Gram Modelling 306 and a Topic modelling on each document to determine concept of a document along. Upon extracting the concept, a weight 308 is assigned to each word in the document for which the concept is extracted. Further, a contribution score 310 may be computed pertaining to another word neighbour to a word in the document. Thus, based on the concept, the weight 308, and the contribution score, the Concept of each document is extracted along with the score 312.

Figure 4:
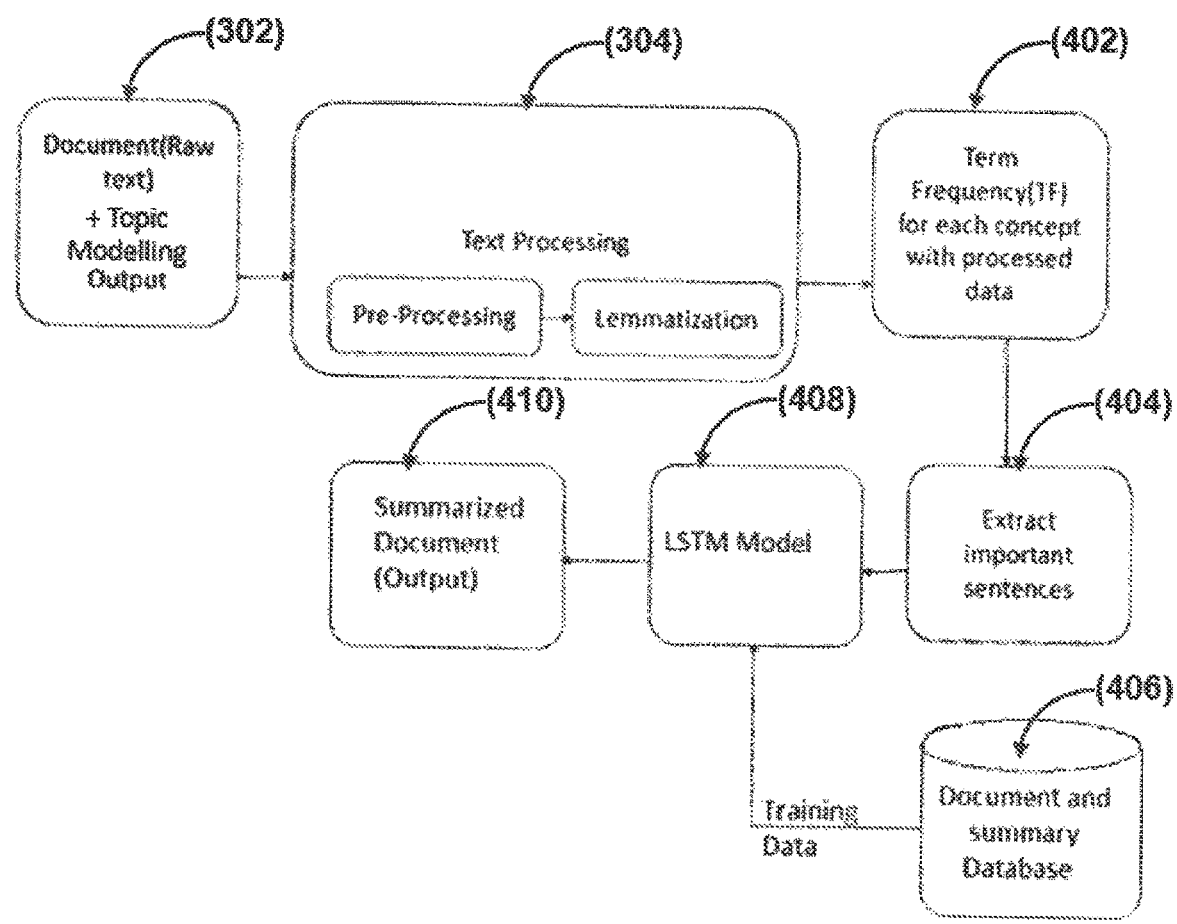

Summarizing includes summarization of the document based on a Term Frequency and training the processor with an artificial recurrent neural network, (RNN) architecture used in Deep Learning including a Long Short-Term Memory (LSTM) model 408. In order words, the documents that have been processed and their 'Concepts' have been deduced move up to summarization. Referring to FIG. 4, the Term Frequency 402 may be performed on each document for which concept has been deduced. Subsequently, important sentences or phrases, contributing to determining the gist of the document, may be extracted 404. These sentences or phrases along with a document and summary database 406 may enable the LSTM model 408 to generate an output i.e. a summarized document 410.

Clustering includes creating a cluster comprising two or more documents having same context. In other words, the clustering of documents heavily eases tasks of finding out what documents can rest contextually closely and what are pretty contextually distant. Since there is a little restriction to the input sources and the corpus to handle documents may be incremental in most cases as the document repositories 220 keep on updating. In one embodiment, the cluster may be created based on a Hybrid Clustering Algorithm. The Hybrid Clustering Algorithm is used to allow the documents to be clustered in a more visually controlled environment. The clusters keep on continuously restructuring based on the visibility comfort of the end user. The parameters may be tuned at any instance/provide a feedback. For example, the initial clusters in a medical domain repository contain documents as 'Cancer Based Documents' and 'Non-Cancer Based Documents'. However, if the user is looking for is a more organ based segregation, the parameters may split and merge the existing clusters to a more zoomed in cluster representation. Thus, this feature enables Dynamic Clusters on an Incremental Corpus, which is a very efficient solution of consolidating documents.

Topic Modelling provides best gist of what the cluster holds based on the weighted concepts. On the weighted concepts, other features may be generated and based on dominant phrase identification; a cluster topic is created. The extraction of these mentioned phrases is done out of the titles of documents.

After all the processing is completed on the document, the documents may be indexed and stored based on the basis of the topics generated in the document repository 220. This ingestion of documents, based on indexing, enables a user to search documents over a query; or find related documents swiftly. It may be noted that during indexing, a need for re-ranking module comes into picture. Whatever ranks of documents to a query the indexer returns; might turn out to be incorrect. In such a scenario, feedback of a Subject Matter Expert (SME) is captured to train a learning algorithm.

Learning to Rank: A Machine Learning algorithm is used to act over the feedback received from the SME. This feedback is used to train the system 102 to generate responses in likeliness to what was voted. It gives better control to SMEs just in case the total processing done till now was not accurately aligned with the expectations of user. In one embodiment, the system 102 may implement a ranking methodology incorporating feedbacks from SMEs to re-rank relevant documents retrieved upon execution of a query.

Thus, based on the above, the Trial Planning and Design module 212 acquires the raw data, from the plurality of disparate data sources and deduces the meaningful information upon pre-processing the raw data using a Natural Language Processing (NLP) approach.

It may be understood that before drafting a Clinical trial protocol design document, the Trial Planning and Design module 212 further inputs the meaningful information, a pre-Drafted protocol, a regulatory authorities' protocol curated by regulatory authorities, and a pre-stored dataset. In one aspect, the pre-stored dataset may comprise queries, pre-asked queries by the regulatory authorities mapped with responses to the pre-asked queries. The Draft Protocol Development and Approval module 214 may process the aforementioned pre-stored dataset for drafting the Clinical trial protocol design document.

In one embodiment, the Draft Protocol Development and Approval module 214 drafts a Clinical trial protocol design document by generating a case frame upon extracting data in form of a key value, from the pre-Drafted protocol and the regulatory authorities protocol, into a standard document. Post generating the case frame, each key value may be validated with the pre-asked queries and the responses in order to compute a predictive value, corresponding to each key value and thereby drafts an interim Clinical trial protocol design document based the predictive value computed for each key value. After the validation each key value, a prediction score may be computed based on overlapping of the interim Clinical trial protocol design document with the pre-Drafted protocol and the regulatory authorities protocol to determine whether the interim Clinical trial protocol design document is approved or rejected. After computing the prediction score, the Clinical trial protocol design document may be generated, when the interim Clinical trial protocol design document is approved based on the prediction score and further approved by the regulatory authorities.

In order to elucidate the above, it may be noted that after generating the case frame, each key extracted may be queried on the query tool. Along with all the information, there is a Regulatory Database with response[s] to queries already recorded by the SMEs for similar queries. All the entries in the new protocol are hence queried and predicted value from these input sources is used to draft the interim Clinical trial protocol design document. In case a completely new key is queried and it has no prediction to hand out then again SMEs provide their input and respective response is logged for future references.

Subsequently, the responses from this querying and the interim Clinical trial protocol design document are overlapped with previous protocols acceptance/rejection status to generate a prediction score. In one aspect, the prediction score is generated to predict whether the interim Clinical trial protocol design document would be approved or rejected. To predict this, a Deep Neural Network (DNN) may be implemented on pre-filed Clinical Trial Documents into being Approved or Rejected. In one aspect, the Draft Protocol Development and Approval module 214 approves the interim Clinical trial protocol design document, when the prediction score is greater than a predefined threshold score. In another aspect, the Draft Protocol Development and Approval module 214 rejects the interim Clinical trial protocol design document when the prediction score is less than a predefined threshold score. Thus, in this manner, the Draft Protocol Development and Approval module 214 drafts the clinical trial protocol design document. It may be noted that the predefined threshold score may be determined upon executing the system 102 with combinations of a plurality of hyper parameters.

The Investigator's Selection and Patient Recruitment module 216 selects an investigator for performing the clinical trial. In one embodiment, the Investigator's Selection and Patient Recruitment module 216 selects the investigator and the patient based on a dataset including, but not limited to, correlation between features, associated to the Clinical trial protocol design document, and features associated to a profile of the investigator or features associated to a profile of the patient, past trials undertaken by investigators, social networking data, historical data of the patient.

Figure 5:
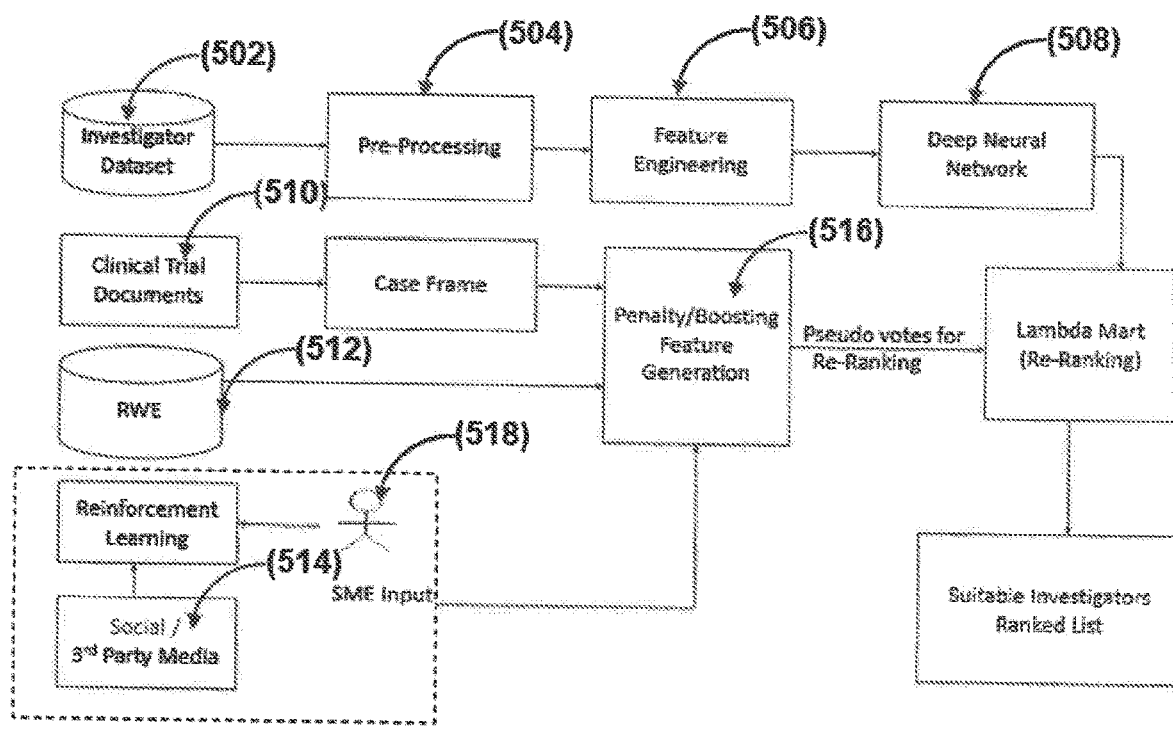

Referring to FIG. 5, indicating selection of the investigator, in accordance with an embodiment of the invention. In order to select the investigator, initially, the aforementioned dataset is fed into the system 102 to select an appropriate investigator. It may be noted that the correlation between features, associated to the Clinical trial protocol design document, and features associated to a profile of the investigator is indicated as an investigator dataset 502. As shown the figure, the investigator dataset 502 is pre-processed, at step 504, to deduce one or more features correlating with the features associated to the Clinical trial protocol design document. This deduction of the one or more features is performed by the feature engineering 506 to assist in selection of the investigator.

In one example, if an Investigator has worked with protocols based only in trials related to Heart Diseases, then that is a negative feature for a new Clinical trial protocol design document based on trial for a Cancer Medication because that is a totally different space of information than the Investigator possesses.

Upon deduction of the one or more features, Deep Neural Network (DNN) is performed, at step 508, on the one or more features for feature classification. It may be noted that this feature classification is trained on various labelled investigator's profile as inputs and then used for first level recommendation to accept the investigator based on an investigator score generated. This investigator score indicates whether the investigator should be selected for the Clinical trial protocol design document.

In addition to the correlation between the features, an investigator may further be selected based on Clinical Trial Documents 510. It may be noted that several clinical trial documents 510 undertaken by the investigators may aid in giving insight of how the investigator has conducted trials, how many trials are approved, if any Criminal Prosecutions/Disqualifications have happened in past. These documents thus contain data in different key value pairs or some other form and hence are extracted from the document using case frame to facilitate the system 102 in selecting an appropriate investigator.

Moreover, Real World Evidence (RWE) data 512 and social media data 514, pertaining to a candidate investigator, may be processed to extract features. In order to deduce feature from the RWE data 512 and the social media data 514, sentiment analysis is performed on the data to determine and classify it as either Penalty or Boost, as shown in block 516. Since some data would be either marginally Penalty or marginally Boost, the system may enable the SME 518 to respond and thereby enabling the system itself from the response captured from the SME 518.

The penalty and boosting features' identification is crucial and exhaustive since the RWE data 512 may be varied, ambiguous so constant learning is essential. Every time the classifier finds information in the ambiguity of whether to put it in the Penalty or Boost type 516; the system 102 prompts the SME 518 for their opinion. The active learning module advises the state predicted is correct and acts as a positive Reward else as a negative Reward. Hem the Reinforcement Learning is basically taking an input of the SME as an Advisor to bring positive and negative rewards for learning.

It may further be noted that system 102 is enabled to actively learn the selection of the investigator based on reinforcement learning technique and Re-Ranking Algorithm implemented on the selection process based on input of the SME 518. In other words, a Machine Learning algorithm is used to act over the inputs of the SME 518. These inputs are used to train the system 102 to generate responses in likeliness. This may provide a better control to the SMEs just in case the total processing done till now was not accurately aligned with the expectations of user. As a result, the Investigator's Selection and Patient Recruitment module 216 may re-rank an Investigator's Profile based on boost and penalty every Investigator earned through all other data sources and thereby enables the system 102 to recommend most appropriate investigator upon considering all the aforementioned parameters.

Figure 6:
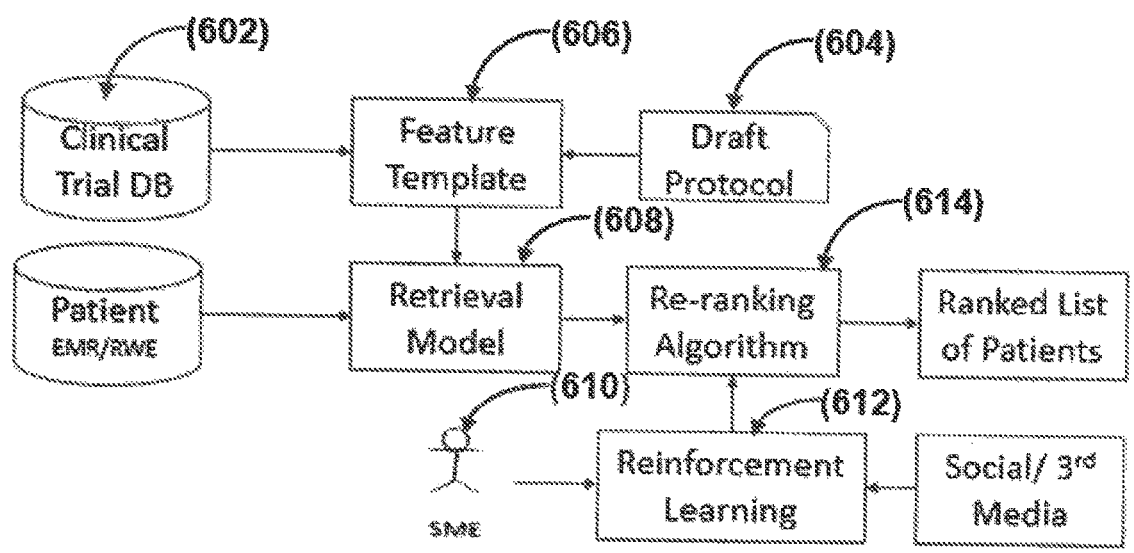

The Investigator's Selection and Patient Recruitment module 216 further selects a patient on which the clinical trial needs to be performed. In one embodiment, the patient may be selected based on correlation between features, associated to the Clinical trial protocol design document, and features associated to a profile of the patient. Referring to FIG. 6, it may be understood that clinical trial dataset 602 pertaining to the clinical trials that have already happened in the past are collated and compared with the Clinical trial protocol design document 604. To enable this, the Custom Named Entity Recognizers, need to be constructed which take feeds from Domain rich information, Taxonomies etc. and extract entities out of the data. The extracted entities may also pose some relations between one another.

The deduced entities from the clinical trial dataset 602 and the Clinical trial protocol design document 604 are used to generate a feature document 606 per document. The feature documents 606 are clustered using a hybrid clustering based on an incremental corpus.

Further, the Investigator's Selection and Patient Recruitment module 216 enables a retrieval model 608 having input of documents that closely represent the Clinical trial protocol design document. Given the number of documents as valid classes, the Investigator's Selection and Patient Recruitment module 216 uses BM25 technique as a probabilistic weighing scheme, a retrieval model or like to compute a closeness score indicating measure the closeness of a patient's profile with the Clinical trial protocol design document. Each patient profile is recommended with documents based on the closeness score. As a result of which, a patient assigned with a highest closeness score is recommended followed by the patient assigned with a second highest closeness score amongst a group of candidate patients.

Further, the Investigator's Selection and Patient Recruitment module 216 performs a Semantic Analysis algorithm on the RWE data 512 and the social media data 514. In one aspect, while performing the semantics analysis, the Investigator's Selection and Patient Recruitment module 216 identifies specific features that might be useful for selecting an appropriate patient in accordance with the Clinical trial protocol design document. Therefore, the Investigator's Selection and Patient Recruitment module 216 extracts the sentiment from the RWE data 512 and the social media data 516, pertaining to a candidate patient, and classify it as either Penalty or Boost. In one aspect, the Investigator's Selection and Patient Recruitment module 216 may enable the SME 610 to input in order to train the system 102 based on a response as provided by the SME 610.

Furthermore, the Investigator's Selection and Patient Recruitment module 216 identifies whether the penalty and boosting features are crucial and exhaustive since the RWE data 512 may be varied and ambiguous. In such a scenario, the Investigator's Selection and Patient Recruitment module 216 prompts the SME 610 to respond. The SME 610 may respond either as positive or negative and thereby enabling the system 102 train itself through reinforcement Learning 612.

In addition to the above, the Investigator's Selection and Patient Recruitment module 216 further implements a Re-Ranking Algorithm 614 that may act over the inputs of the SME 610. These inputs may be used to train the system 102 to generate responses in likeliness to what was voted and gives a better control to the SMEs 610 to accurately aligned with the expectations.

Thus, in this manner, the Investigator's Selection and Patient Recruitment module 216 facilitates to select the investigator, for performing the clinical trial, and the patient on which the clinical trial needs to be performed.

Figure 7:
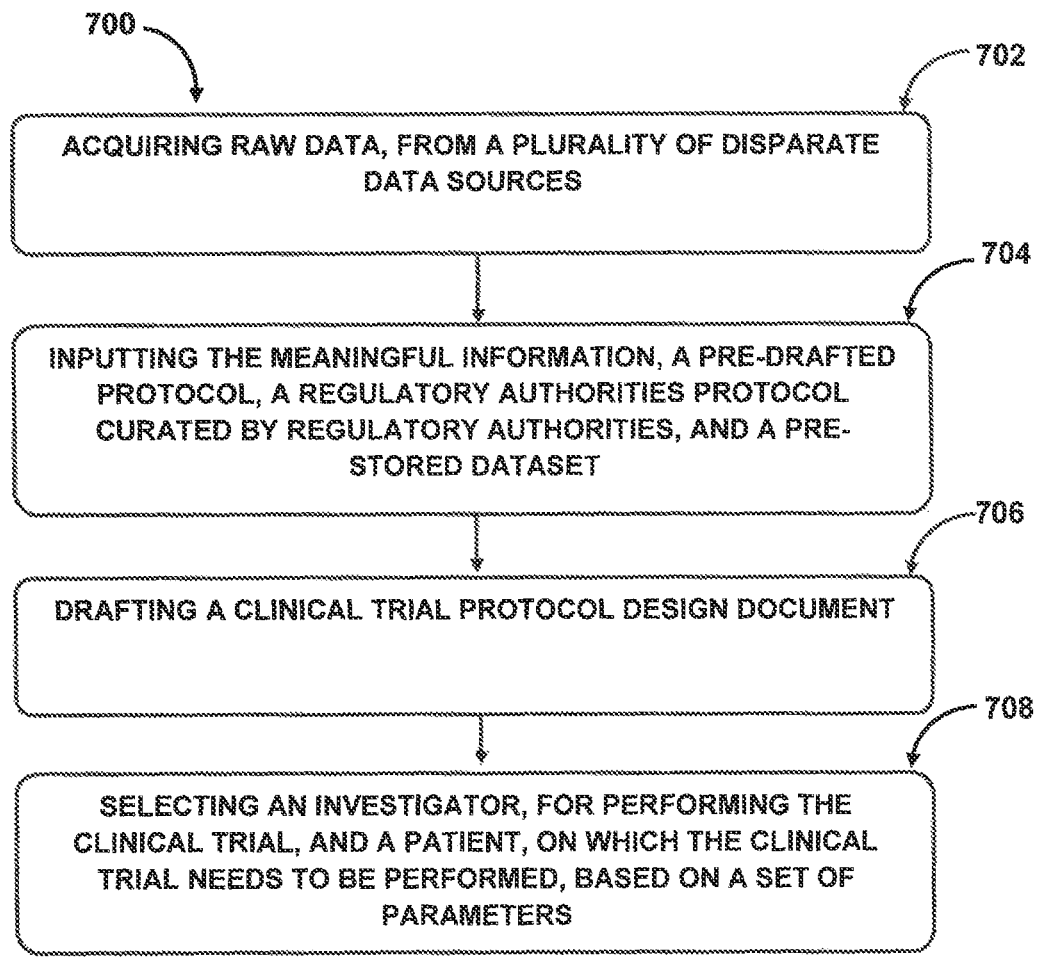
FIGS. 7 and 8 illustrate a method for generating the clinical trial protocol design, thereby selecting the Patient and the Investigator, in accordance with an embodiment of the present subject matter.

Referring now to FIG. 7, a method 700 for generating Clinical trial protocol design document thereby selecting a Patient and an Investigator for a clinical trial process, in accordance with an embodiment of the present subject matter. The method 700 may be described in the general context of computer executable instructions. Generally, computer executable instructions can include routines, programs, objects, components, data structures, procedures, modules, functions, etc., that perform particular functions or implement particular abstract data types. The method 700 may also be practiced in a distributed computing environment where functions are performed by remote processing devices that are linked through a communications network. In a distributed computing environment, computer executable instructions may be located in both local and remote computer storage media, including memory storage devices.

The order in which the method 700 is described is not intended to be construed as a limitation, and any number of the described method blocks can be combined in any order to implement the method 700 or alternate methods. Additionally, individual blocks may be deleted from the method 700 without departing from the spirit and scope of the subject matter described herein. Furthermore, the method can be implemented in any suitable hardware, software, firmware, or combination thereof. However, for ease of explanation, in the embodiments described below, the method 700 may be considered to be implemented as described in the system 102.

At block 702, raw data, from a plurality of disparate data sources, may be acquired. In one aspect, the raw data may comprise a set of documents. It may be understood that the raw data is being pre-processed to deduce meaningful information. In one implementation, the raw data may be acquired by the Trial Planning and Design module 212.

At block 704, a pre-Drafted protocol, a regulatory authorities' protocol curated by regulatory authorities, and a pre-stored dataset may be inputted. In one aspect, the pre-stored dataset may comprise queries, pre-asked queries by the regulatory authorities mapped with responses to the pre-asked queries. In one implementation, the pre-Drafted protocol, the regulatory authorities' protocol curated by regulatory authorities, and the pre-stored dataset may be inputted by the Trial Planning and Design module 212.

At block 706, a Clinical trial protocol design document may be drafted. In one implementation, the Clinical trial protocol design document may be drafted by the Draft Protocol Development and Approval 214.

At block 708, an investigator, for performing the clinical trial, and a patient, on which the clinical trial needs to be performed may be selected based on a set of parameters. In one aspect, the set of parameters may comprise correlation between features, associated to the Clinical trial protocol design document, and features associated to a profile of the investigator or features associated to a profile of the patent, past trials undertaken by investigators, social networking data, historical data of the patient. In one implementation, the investigator and the patient may be selected by the Investigator's Selection and Patient Recruitment module 216.

Figure 8:
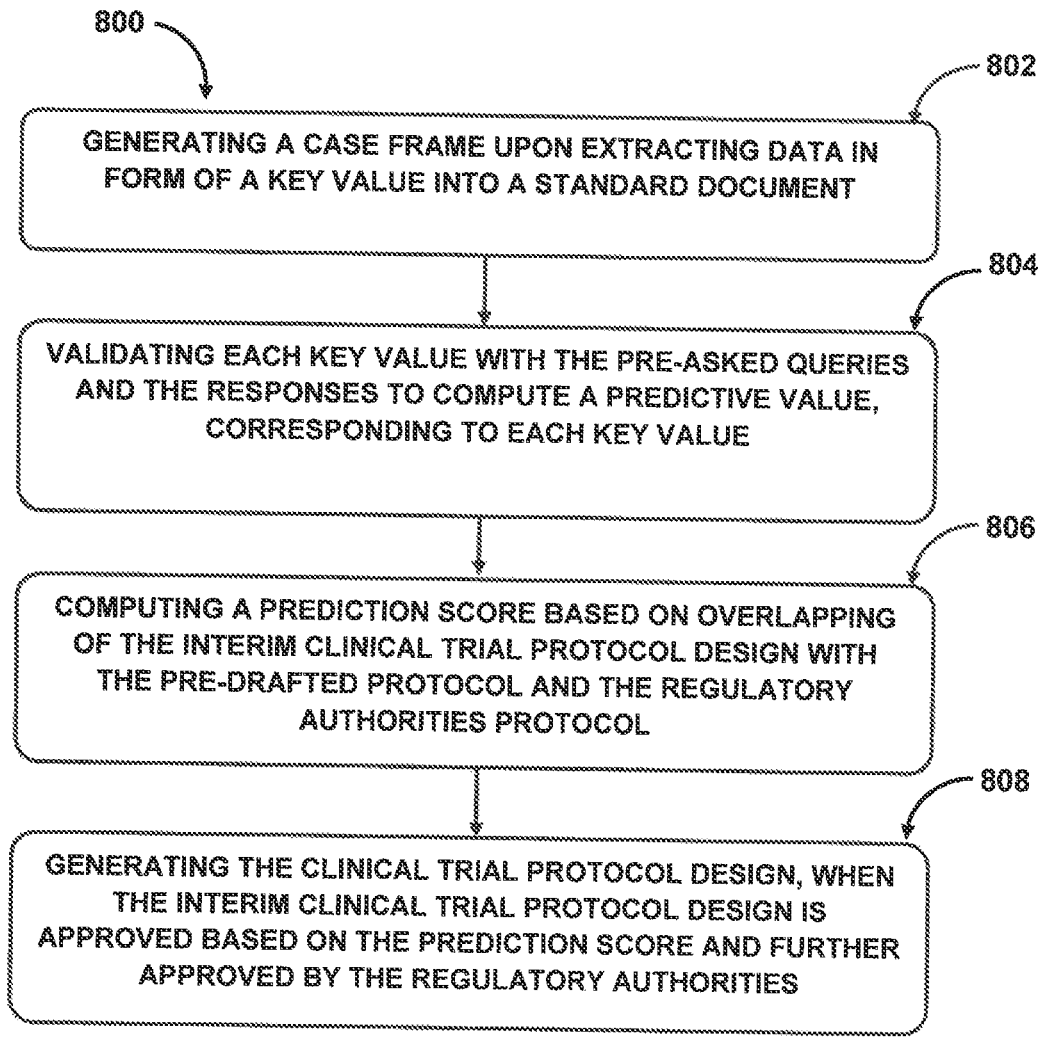

Referring now to FIG. 8, a method 800 for drafting the Clinical trial protocol design document, in accordance with an embodiment of the present subject matter. The method 800 may be described in the general context of computer executable instructions. Generally, computer executable instructions can include routines, programs, objects, components, data structures, procedures, modules, functions, etc., that perform particular functions or implement particular abstract data types. The method 800 may also be practiced in a distributed computing environment where functions are performed by remote processing devices that are linked through a communications network. In a distributed computing environment, computer executable instructions may be located in both local and remote computer storage media, including memory storage devices.

The order in which the method 800 is described is not intended to be construed as a limitation, and any number of the described method blocks can be combined in any order to implement the method 800 or alternate methods. Additionally, individual blocks may be deleted from the method 800 without departing from the spirit and scope of the subject matter described herein. Furthermore, the method can be implemented in any suitable hardware, software, firmware, or combination thereof. However, for ease of explanation, in the embodiments described below, the method 800 may be implemented as described in the system 102.

At block 802, a case frame may be generated upon extracting data in form of a key value into a standard document. In one aspect, the key value may be extracted from the pre-Drafted protocol and the regulatory authorities' protocol. In one implementation, the case frame may be generated by the Draft Protocol Development and Approval 214.

At block 804, each key value may be validated with the pre-asked queries and the responses to compute a predictive value, corresponding to each key value, thereby drafting an interim Clinical trial protocol design document based the predictive value computed for each key value. In one implementation, each key value may be validated by the Draft Protocol Development and Approval 214.

At block 806, a prediction score may be computed based on overlapping of the interim Clinical trial protocol design document with the pre-Drafted protocol and the regulatory authorities protocol to determine whether the interim Clinical trial protocol design document is approved or rejected. In one implementation, the prediction score may be computed by the Draft Protocol Development and Approval 214.

At block 808, the Clinical trial protocol design document may be generated, when the interim Clinical trial protocol design document is approved based on the prediction score and further approved by the regulatory authorities. In one implementation, the Clinical trial protocol design document may be generated by the Draft Protocol Development and Approval 214.

In one embodiment, practical implementation of the system 102 may include generating a Clinical trial protocol design document for testing a therapeutic effect of a medicine upon selecting a patient on which the clinical trial needs to be performed. It may be noted that the generation of the Clinical trial protocol design template and the selection of the patient may be performed by the system 102 using AI/ML approaches. More specifically, the Clinical trial protocol design document indicates an objective, design, methodology, statistical considerations while performing the clinical trial. It may be noted that the Clinical trial protocol design document usually provides a background and a rationale for the clinical trial process.

Although implementations for methods and systems for generating Clinical trial protocol design document thereby selecting a Patient and an Investigator for a clinical trial process have been described in language specific to structural features and/or methods, it is to be understood that the appended claims are not necessarily limited to the specific features or methods described. Rather, the specific features and methods are disclosed as examples of implementations for generating the Clinical trial protocol design document thereby selecting the Patient and the Investigator.

The invention claimed is:

1. A method for generating a clinical trial protocol design document, thereby selecting a patient and an investigator for a clinical trial process, the method comprising:

acquiring, by a processor, raw data, from a plurality of disparate data sources comprising a set of documents, wherein the raw data is being pre-processed to create one or more context-based clusters based on a Hybrid Clustering Algorithm, wherein each of the one or more context-based clusters comprises one or more of the set of documents having a same context, wherein the one or more context-based clusters are created by preprocessing the raw data, and wherein the pre-processing further comprises:

removing at least one of a stop word and a special character from each document of the set of documents thereby generating one or more lemmas to make the raw data executable for a Natural Language Processing (NLP) technique;

identifying a plurality of named entities from the raw data, upon executing the NLP technique, to determine a domain pertaining to each document;

performing at least one of an N-Gram modelling and a topic modelling on each document to determine a concept of a document along with a score, wherein the concept and the score are determined by computing a weighted score pertaining to a word in the document, and a contribution score pertaining to another word neighbour to the word;

summarizing the document based on a term frequency and training the processor with an artificial recurrent neural network, (RNN) architecture used in deep learning including a Long Short-Term Memory (LSTM) model; and storing each document, in the document repository, under the one or more context-based clusters thereby enabling a user to search the one or more of the set of documents through a query;

receiving, by the processor, the one or more context-based clusters, a pre-drafted protocol, a regulatory authorities protocol curated by regulatory authorities, and a pre-stored dataset, present in a document repository coupled with the processor, wherein the pre-stored dataset comprises queries and pre-asked queries by the regulatory authorities mapped with responses to the pre-asked queries;

drafting, by the processor, a clinical trial protocol design document by:

extracting data in a form of a key value, from the pre-drafted protocol and the regulatory authorities protocol, forming a standard document with the extracted data, validating the extracted data by comparing the extracted data with the pre-asked queries on a query tool, and the responses to the pre-asked queries, to compute a predictive value, corresponding to each key value, drafting an interim clinical trial protocol design document based on the computed predictive value computed for each key value, computing a prediction score by implementing a Deep Neural Network (DNN) algorithm and determining acceptance or rejection status of the interim clinical trial protocol design document based on correlation among the interim clinical trial protocol design document, the pre-drafted protocol and the regulatory authorities protocols, and generating the clinical trial protocol design document, based on the acceptance status of the interim clinical trial protocol design document; and selecting, by the processor, an investigator, for performing the clinical trial, and a patient, on which the clinical trial needs to be performed, based on a set of parameters, wherein the set of parameters comprise correlation between features, associated with the clinical trial protocol design document, and features associated to a profile of the investigator or features associated to a profile of the patient, past trials undertaken by investigators, social networking data, or historical data of the patient.

2. The method of claim 1, wherein the clinical trial protocol design document is generated for testing a therapeutic effect of a medicine upon selecting a patient on which the clinical trial needs to be performed, and wherein the generation of the clinical trial protocol design document and the selection of the patient is performed based on artificial intelligence and machine learning approaches.

3. The method of claim 1, wherein the interim clinical trial protocol design document is approved when the prediction score is greater than a predefined threshold score, and wherein the interim clinical trial protocol design document is rejected when the prediction score is less than a predefined threshold score, and wherein the predefined threshold score is determined upon executing the processor with combinations of a plurality of hyper parameters.

4. The method of claim 1, wherein each investigator, available in an investigator dataset, is assigned with a recommendation score upon performing the Deep Neural Network algorithm on the correlation between the features, associated to the clinical trial protocol design document, and the features associated to the profile of the investigator.

5. The method of claim 1, wherein the processor is further enabled to actively learn the selection of the investigator based on a reinforcement learning technique and Re-Ranking Algorithm implemented on the selection process based on an input received from a Subject Matter Expert (SME).

6. A non-transitory computer readable medium embodying a program executable in a computing device for method for generating a clinical trial protocol design document thereby selecting a patient and an investigator for a clinical trial process, the program comprising a program code, wherein the program code comprises:

a program code for acquiring raw data, from a plurality of disparate data sources comprising a set of documents, wherein the raw data is being pre-processed to create one or more context-based clusters based on a Hybrid Clustering Algorithm, wherein each of the one or more context-based clusters comprises one or more of the set of documents having a same context, wherein the one or more context-based clusters are created by pre-processing the raw data, and wherein the pre-processing further comprises:

removing at least one of a stop word and a special character from each document of the set of documents thereby generating one or more lemmas to make the raw data executable for a Natural Language Processing (NLP) technique;

identifying a plurality of named entities from the raw data, upon executing the NLP technique, to determine a domain pertaining to each document;

performing at least one of an N-Gram modelling and a topic modelling on each document to determine a concept of a document along with a score, wherein the concept and the score are determined by computing a weighted score pertaining to a word in the document, and a contribution score pertaining to another word neighbour to the word;

summarizing the document based on a term frequency and training the processor with an artificial recurrent neural network, (RNN) architecture used in deep learning including a Long Short-Term Memory (LSTM) model; and storing each document, in the document repository, under the one or more context-based clusters thereby enabling a user to search the one or more of the set of documents through a query;

a program code for receiving the one or more context-based clusters, a pre-drafted protocol, a regulatory authorities protocol curated by regulatory authorities, and a pre-stored dataset, present in a document repository coupled with the processor, wherein the pre-stored dataset comprises queries and pre-asked queries by the regulatory authorities mapped with responses to the pre-asked queries;

a program code for drafting a clinical trial protocol design document by, extracting data in a form of a key value, from the pre-drafted protocol and the regulatory authorities protocol, forming a standard document with the extracted data, validating the extracted data by comparing the extracted data with the pre-asked queries on a query tool, and the responses to the pre-asked queries, to compute a predictive value, corresponding to each key value, drafting an interim clinical trial protocol design document based on the computed predictive value computed for each key value, computing a prediction score by implementing a Deep Neural Network (DNN) algorithm and determining acceptance or rejection status of the interim clinical trial protocol design document based on correlation among the interim clinical trial protocol design document, the pre-drafted protocol and the regulatory authorities protocols; and generating the clinical trial protocol design document, based on the acceptance status of the interim clinical trial protocol design; and a program code for selecting an investigator, for performing the clinical trial, and a patient, on which the clinical trial needs to be performed, based on a set of parameters, wherein the set of parameters comprises correlation between features, associated with the clinical trial protocol design document, and features associated to a profile of the investigator or features associated to a profile of the patient, past trials undertaken by investigators, social networking data, historical data of the patient.

7. A system for generating a clinical trial protocol design document, thereby selecting a patient and an investigator for a clinical trial process, the system comprising:

a processor; and a memory coupled to the processor, wherein the processor is capable of executing a plurality of modules stored in the memory, and wherein the plurality of modules comprise:

a Trial Planning and Design module for:

acquiring raw data, from a plurality of disparate data sources comprising a set of documents, wherein the raw data is being pre-processed to create one or more context-based clusters based on a Hybrid Clustering Algorithm, wherein each of the one or more context-based clusters comprises one or more of the set of documents having a same context, wherein the one or more context-based clusters are created by pre-processing the raw data, and wherein the pre-processing further comprises:

removing at least one of a stop word and a special character from each document of the set of documents thereby generating one or more lemmas to make the raw data executable for a Natural Language Processing (NLP) technique;

identifying a plurality of named entities from the raw data, upon executing the NLP technique, to determine a domain pertaining to each document;

performing at least one of an N-Gram modelling and a topic modelling on each document to determine a concept of a document along with a score, wherein the concept and the score are determined by computing a weighted score pertaining to a word in the document, and a contribution score pertaining to another word neighbour to the word;

summarizing the document based on a term frequency and training the processor with an artificial recurrent neural network, (RNN) architecture used in deep learning including a Long Short-Term Memory (LSTM) model; and storing each document, in the document repository, under the one or more context-based clusters thereby enabling a user to search the one or more of the set of documents through a query;

receiving the one or more context-based clusters, a pre-drafted protocol, a regulatory authorities protocol curated by regulatory authorities, and a pre-stored dataset, present in a document repository coupled with the processor, wherein the pre-stored dataset comprises queries and pre-asked queries by the regulatory authorities mapped with responses to the pre-asked queries;

a Draft Protocol Development and Approval module for drafting a clinical trial protocol design document by, extracting data in a form of a key value, from the pre-drafted protocol and the regulatory authorities protocol, forming a standard document with the extracted data, validating the extracted data by comparing the extracted data with the pre-asked queries on a query tool, and the responses to the pre-asked queries, to compute a predictive value, corresponding to each key value, drafting an interim clinical trial protocol design document based on the computed predictive value computed for each key value, computing a prediction score by implementing a Deep Neural Network (DNN) algorithm and determining acceptance or rejection status of the interim clinical trial protocol design document based on correlation among the interim clinical trial protocol design document, the pre-drafted protocol and the regulatory authorities protocols, and generating the clinical trial protocol design document, based on the acceptance status of the interim clinical trial protocol design document; and an Investigator's Selection and Patient Recruitment module for selecting an investigator, for performing the clinical trial, and a patient, on which the clinical trial needs to be performed, based on a set of parameters, wherein the set of parameters comprises correlation between features, associated to the clinical trial protocol design document, and features associated to a profile of the investigator or features associated with a profile of the patient, past trials undertaken by investigators, social networking data, or historical data of the patient.

8. The system of claim 7, wherein the system generates the clinical trial protocol design document for testing a therapeutic effect of a medicine upon selecting a patient on which the clinical trial needs to be performed, wherein the generation of the clinical trial protocol design document and the selection of the patient is performed based on Artificial Intelligence and Machine learning approaches.

9. The system of claim 7, wherein the Draft Protocol Development and Approval module approves the interim clinical trial protocol design document, when the prediction score is greater than a predefined threshold score, and wherein the interim clinical trial protocol design document is rejected when the prediction score is less than a predefined threshold score.

10. The system of claim 7, wherein the Investigator's Selection and Patient Recruitment module assigns each investigator, available in an investigator dataset, with a recommendation score upon performing the Deep Neural Network algorithm on the correlation between the features, associated to the clinical trial protocol design document, and the features associated to the profile of the investigator.

11. The system of claim 7, wherein the processor is further enabled to actively learn the selection of the investigator based on a reinforcement learning technique and Re-Ranking Algorithm implemented on the selection process based on an input received from a Subject Matter Expert (SME).

* * * * *